US006684883B1

(12) United States Patent
Burns

(10) Patent No.: US 6,684,883 B1
(45) Date of Patent: Feb. 3, 2004

(54) NASAL CANNULA HEADBAND APPARATUS

(76) Inventor: Bonnie C. Burns, 945 S. 6th St., Lander, WY (US) 82520

( * ) Notice: Subject to any disclaimer, the term of this patent is extended or adjusted under 35 U.S.C. 154(b) by 190 days.

(21) Appl. No.: 09/934,160

(22) Filed: Aug. 21, 2001

(51) Int. Cl.$^7$ ............................................. A61M 15/08
(52) U.S. Cl. ............................ 128/207.18; 128/206.11; 128/DIG. 26
(58) Field of Search ........................ 128/203.22, 204.11, 128/206.11, 207.18, DIG. 26

(56) References Cited

U.S. PATENT DOCUMENTS

| | | | | |
|---|---|---|---|---|
| 853,431 | A | * 5/1907 | Allen | 128/207.18 |
| 853,439 | A | * 5/1907 | Clark | 128/207.18 |
| 1,155,608 | A | * 10/1915 | Nieschang | 128/203.22 |
| 2,007,287 | A | * 7/1935 | Shotton | 128/203.22 |
| 2,168,705 | A | 8/1939 | Francisco et al. | 128/206 |
| 2,208,633 | A | * 7/1940 | Heidbrink | 128/203.28 |
| 2,259,817 | A | 10/1941 | Hawkins | 128/206 |
| 2,292,568 | A | * 8/1942 | Kanter et al. | 128/203.28 |
| 2,590,006 | A | * 3/1952 | Gordon | 604/180 |
| 2,763,263 | A | * 9/1956 | Ellman | 128/203.13 |
| 3,209,755 | A | * 10/1965 | McCarthy et al. | 604/174 |
| 3,726,275 | A | 4/1973 | Jackson et al. | 128/206 |
| 3,802,431 | A | * 4/1974 | Farr | 128/207.18 |
| 4,018,221 | A | * 4/1977 | Rennie | 128/207.18 |
| 4,106,505 | A | * 8/1978 | Salter et al. | 128/207.18 |
| 4,122,857 | A | * 10/1978 | Haerr | 604/180 |
| 4,156,426 | A | 5/1979 | Gold | 128/205 |
| 4,282,871 | A | 8/1981 | Chodrow et al. | 128/207.18 |
| 4,284,076 | A | 8/1981 | Hall | 128/207.18 |
| 4,406,283 | A | 9/1983 | Bir | 128/207.18 |
| 4,465,067 | A | 8/1984 | Koch et al. | 128/207.18 |
| 4,480,639 | A | * 11/1984 | Peterson et al. | 128/207.18 |
| 4,559,941 | A | * 12/1985 | Timmons et al. | 128/207.18 |
| 4,641,647 | A | 2/1987 | Behan | 128/207.18 |
| 4,648,398 | A | * 3/1987 | Agdanowski et al. | 128/207.18 |
| 4,665,566 | A | 5/1987 | Garrow | 2/171 |
| 4,708,446 | A | * 11/1987 | Timmons et al. | 351/158 |
| 4,739,757 | A | 4/1988 | Edwards | 128/207.18 |
| 4,753,233 | A | * 6/1988 | Grimes | 128/207.18 |
| 4,774,946 | A | 10/1988 | Ackerman et al. | 128/207.18 |
| 4,808,160 | A | 2/1989 | Timmons et al. | 604/94 |
| 4,836,200 | A | 6/1989 | Clark | 128/207.18 |
| 4,915,105 | A | * 4/1990 | Lee | 128/205.27 |
| 4,944,310 | A | * 7/1990 | Sullivan | 128/848 |
| 4,996,983 | A | * 3/1991 | AmRhein | 128/206.11 |
| 5,005,571 | A | * 4/1991 | Dietz | 128/205.25 |
| 5,113,857 | A | * 5/1992 | Dickerman et al. | 128/207.18 |
| 5,117,818 | A | * 6/1992 | Palfy | 128/204.11 |
| 5,188,101 | A | 2/1993 | Tumolo | 128/207.18 |
| 5,269,296 | A | 12/1993 | Landis | 128/207.18 |
| 5,271,391 | A | * 12/1993 | Graves | 128/207.18 |
| 5,438,979 | A | * 8/1995 | Johnson et al. | 128/207.18 |
| 5,468,229 | A | * 11/1995 | Chandler | 604/179 |
| 5,496,282 | A | * 3/1996 | Militzer et al. | 604/179 |
| 5,538,000 | A | 7/1996 | Rudolph | 128/205.25 |
| 5,558,090 | A | 9/1996 | James | 128/207.18 |
| 5,636,630 | A | 6/1997 | Miller et al. | 128/207.17 |
| 5,645,058 | A | 7/1997 | Odom | 128/207.18 |
| 6,119,694 | A | 9/2000 | Correa et al. | 128/207.13 |

* cited by examiner

Primary Examiner—Aaron J. Lewis
(74) Attorney, Agent, or Firm—Dorsey & Whitney LLP; Shane P. Coleman

(57) ABSTRACT

A nasal cannula headband apparatus is disclosed having a headband portion and a nasal cannula system connected thereto. The headband portion has a soft, lightweight, non-elastic, water-resistant headband that wraps around a user's head. The headband is held in place using a headband connecting portion. The headband has an inner side that helps hold the headband apparatus to the user's head by friction and an outer side that is smoother than the inner side and allows the headband to slide against pillows, sheets, bedding, and other materials without becoming dislodged from the patient's head. The cannula system connects to a supply of breathable gas and delivers the gas to the patient's nostrils and has a pair of cannula tubes fixedly attached to the outer side of the headband by fasteners that keep the cannula tubes in place relative to the headband and direct the cannula tubes behind the patient's ears.

21 Claims, 5 Drawing Sheets

NASAL CANNULA HEADBAND APPARATUS

FIELD OF INVENTION

The invention relates generally to a nasal cannula apparatus for the delivery of a gas, such as air, to a person's nostrils. More particularly, it relates to a headband cannula apparatus that secures a cannula tube to an individual's head.

BACKGROUND

In the field of oxygen delivery systems, various systems are known for delivering gas, such as air or oxygen, from a supply tank to a patient via a cannula tube system. Such systems include nasal cannula apparatuses comprising one or more tubes that attach to a tank and provide oxygen to a patient via the patient's nostrils. A typical system might include a cannula trunk tube that connects to an oxygen tank and splits into two nasal cannula tubes. In a typical system, the cannula tubes may drape over the ears of the patient and lead to nostril tubes that direct air into the nostrils of the patient. In other existing systems, the tubes may go in front of the patient rather than passing behind the patient's ears. Near the patient's nose, the pair of cannula tubes may come together in a physical apparatus, such as a cannula junction, that directs the air into the nostril tubes. For example, a cannula junction may be used as a bridge to hold the cannula tubes in place and to direct the tubes into separate nostril tubes referred to as nasal extensions. In another example, the tubes may be directed into a mask that covers the patient's nose or the patient's nose and mouth.

It is desirable to keep the cannula tubes away from the patient's face so that the system is less cumbersome. It is also desirable to hold the cannula tubes in place relative to the patient's nose so that air to the patient is not cut off. In particular, it is desirable to hold the tubes in place and to keep the tubes out of the patient's way while the patient is sleeping, bathing, eating, or simply moving about in public.

Various methods are known for securing a cannula tube system to a patient's head to make use of the cannula tube system more convenient. Such systems include systems using a hat or cap support structure or an eyeglass-type frame structure. Such structures may be inconvenient for some users who do not like to wear caps or glasses, and may be inconvenient while sleeping, bathing, etc.

Other systems include Velcro headband systems in which the cannula tubes are releasably connected to a headband by one or more strips of a hook-and-loop type fastener, such as a Velcro product. Still other systems use headbands that either go around the user's head or over the top or crown portion of the head. Existing headband systems leave many of the users' needs unmet. Systems that go over the top of the head or crown portion of the head may be cumbersome to some users by rearranging the user's hair or by interfering with other devices such as hats, for example. This is particularly true of systems in which the top strap going over the top at the head is fixed or tight in position. Other headband systems still have deficiencies such as the inability to slide against sheets, pillows, or other bedding, for example while the user is sleeping, without becoming dislodged from the user's head. Some headband systems absorb water or otherwise deform or stretch when the headband becomes wet, for example while bathing. Some headbands are made from a heavy material, such as leather, which can be cumbersome for some patients. Some headband systems have complicated schemes that require the user to thread the cannula tubes through the headband portion or to attach the cannula tubes to the headband portion if the cannula tube is a separate, removable item from the headband. This may be particularly difficult for older patients who may have arthritis or other medical conditions that make it difficult to fasten the cannula tubes to the headband or to thread it through the headband. This also presents a problem with hook-and-loop systems that require the patient to connect portions of the headband system.

What is needed is a more convenient headband cannula system for distributing a breathable gas to the patient. In particular, what is needed is a disposable headband system that is convenient and that allows the user to use the headband while sleeping, bathing, and going out in public.

SUMMARY OF INVENTION

A nasal cannula headband apparatus is disclosed having a headband portion and a nasal cannula system connected thereto. The headband portion has a soft, lightweight, non-elastic, water-resistant headband that wraps around a patient's head. The headband is held in place using a headband connecting portion. The headband has an inner side that helps hold the headband apparatus to the patient's head by friction and an outer side that is smoother than the inner side and allows the headband to slide against pillows, sheets, bedding, and other materials without becoming dislodged from the patient's head. The cannula system connects to a supply of breathable gas and delivers the gas to the patient's nostrils. The cannula system has a pair of cannula tubes that are fixedly attached to the outer side of the headband by fasteners and lead to a cannula junction above the patient's nose. From the cannula junction, the gas is directed downwardly toward the patient's nostrils. The fasteners keep the cannula tubes in place relative to the headband and direct the cannula tubes behind the patient's ears.

In one embodiment, the cannula tubes are attached to the outside of the headband portion in such a manner to allow the tubes to run longitudinally with respect to the headband, along the sides of the user's head. In another embodiment, one or more cannula tubes fixedly attach only to the front portion of the headband and to the back portion of the headband, and pass over the top of the user's head.

DETAILED DESCRIPTION

Figure 1:
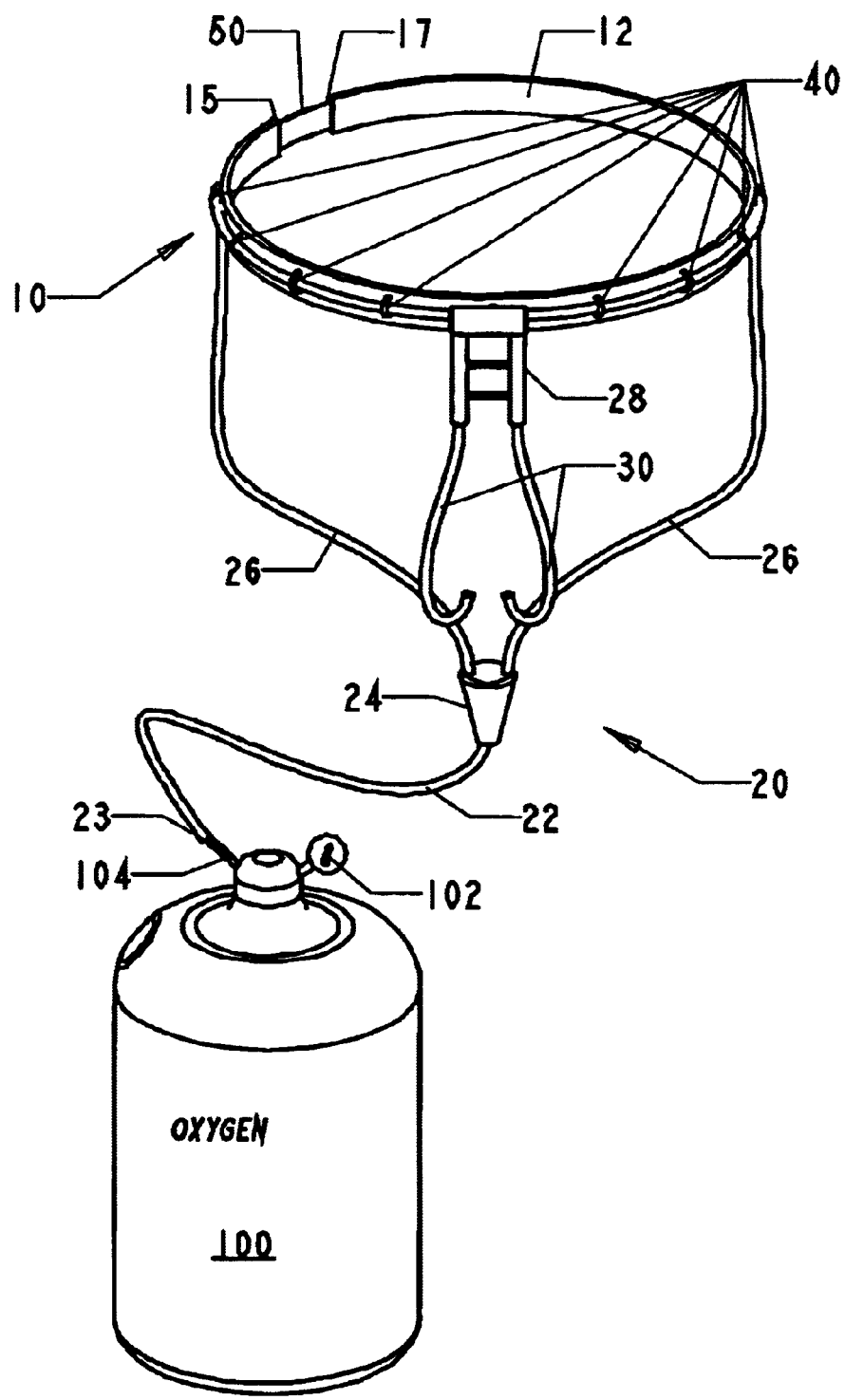
FIG. 1 shows the nasal cannula headband attached to an air supply.

FIG. 1 shows a nasal cannula headband apparatus 10 connected to a supply of a breathable gas 100, such as an oxygen tank 100. The headband apparatus 10 comprises a headband 12 having first and second ends 15, 17, which are connected to a headband connecting portion 50. The gas supply 100 may have a gauge 102 and a nozzle 104 for regulating the dispensation of the gas. The headband apparatus 10 is connected to a nasal cannula system 20 that delivers a gas to the user's nose. In the example of FIG. 1, the nasal cannula system comprises a cannula trunk 22, a trunk junction 24, a pair of cannula tubes 26, a cannula junction 28, and a pair of nasal extensions 30. In one embodiment, the cannula trunk 22, the cannula tubes 26, and the nasal extensions 30 may each be made from flexible plastic tubing having an inside diameter of approximately 0.25 inches, the cannula tubes 26 may be a flexible tubing, having respective inside diameters of 0.25 inches, 0.125 inches, and 0.0625 inches. The cannula tubes 26, cannula junction 28, trunk junction 24, cannula trunk 22, and nasal extensions 30 may be formed from a single piece of contiguous material or they may each be separate pieces, which may be removeably or permanently connected to each other as shown.

The headband apparatus 10 has a cannula trunk 22 and a pair of cannula tubes 26. The cannula trunk 22 has an inlet end 23 connected to a nozzle 104 on the air supply 100. The cannula trunk 22 also has a second end comprising a trunk junction 24, which connects the trunk 22 to cannula tubes 26. The cannula tubes 26 are securely fastened to a headband 12 by one or more fasteners 40. The fasteners 40 may be, for example, stitching around the outside of the cannula tube 26. The fasteners 40 are positioned such that the cannula tube 26 is securely held behind a user's ear. The cannula tubes 26 drop behind the ear where they are kept out of the user's way. The cannula tubes 26 enter a cannula junction 28. The cannula junction 28 directs the gas toward the user's nose. The cannula junction 28 may have a pair of nasal extensions 30 which receive air from the cannula junction 28 and direct the air into the patient's nostrils.

The headband 12 may be made of a breathable fabric that permits air to pass through it to the user's head. The headband 12 may be made of a waterproof material in that allows the headband 12 to become wet without changing shape substantially—for example, when a patient is bathing. The headband 12 may be made from a soft or cushiony material for a comfortable fit around a user's head. The inner side may be of a greater friction than the outer side so that friction causes the headband 12 to stay securely about the user's head. The outer side of the headband 12 may be of a smoother surface. Such outer side may be slidable relative to other fabrics; for example, bedding. The headband 12 is designed such that it stays substantially in place around a patient's head while the user is sleeping, even as the user moves around during sleep. In one embodiment, the headband 12 is a non-elastic material and is held securely about the user's head by a headband connecting portion 50. The headband connecting portion 50 may be an elastic portion, a hook-and-loop fastener, or any other suitable connector that holds the headband apparatus 10 around the circumference of a patient's head. The headband connecting portion 50 may be positioned near the back of a user's head. In one embodiment, the headband connecting portion 50 is off-center with respect to the back of the user's head for greater comfort. In one embodiment, the headband is approximately 1.5 to 2.0 inches wide, and is constructed using a product manufactured by Velcro USA, Inc. under the models numbers 672, 3610, 3984, or 3900.

Figure 2:
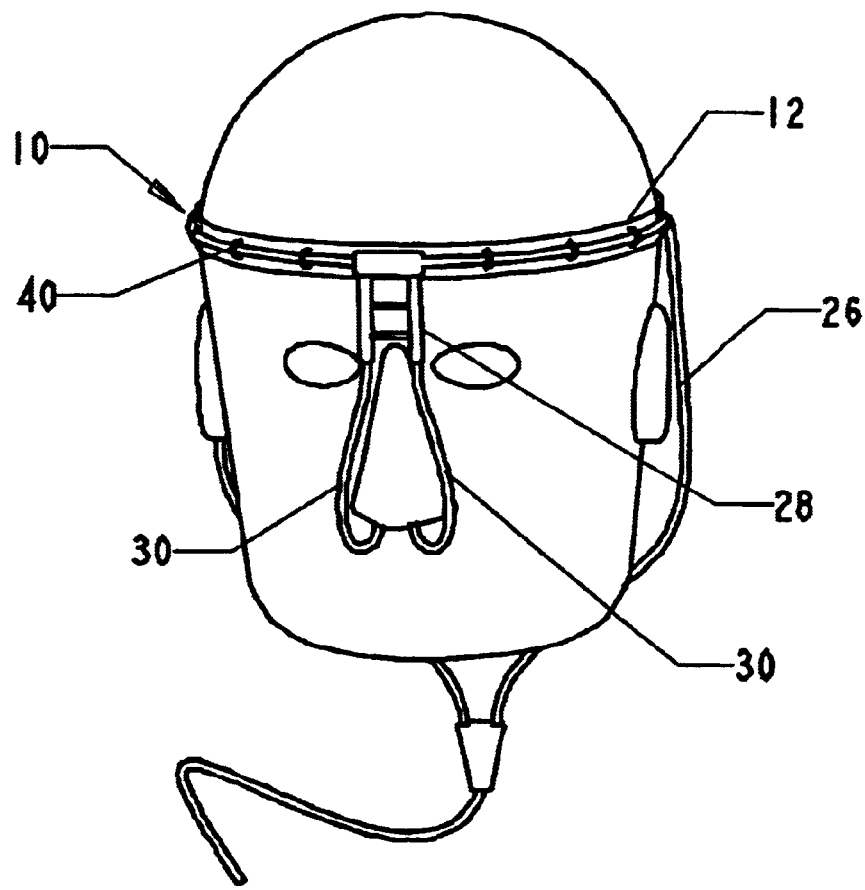
FIG. 2 shows the front portion of the apparatus in use on a person.

FIG. 2 shows the headband apparatus 10 in use about a patient's head. In the embodiment shown, the headband apparatus 10 passes around a circumference of the patient's head. FIG. 2 shows a front view of the headband 12 and the pair of cannula tubes 26 securely fastened by fasteners 40 to the headband 12. The cannula tubes 26 run generally parallel to the headband 12 along the front portion of the headband 12, where the fasteners 40 connect it. The cannula tubes 26 connect to a cannula unction 28 above the bridge of the patient's nose. The cannula junction 28 directs the breathable gas into the patient's nostrils via nasal extensions 30. As shown in FIG. 2, the cannula tubes 26 are fastened to the headband 12 such that the tubes 26 pass behind the patient's ears for greater comfort. The headband 12 may be made from a substantially non-elastic material to enable cannula tubes 26 to be fixedly connected to the headband 12 so that the cannula tubes 26 do not slide relative to the headband.

Figure 3:
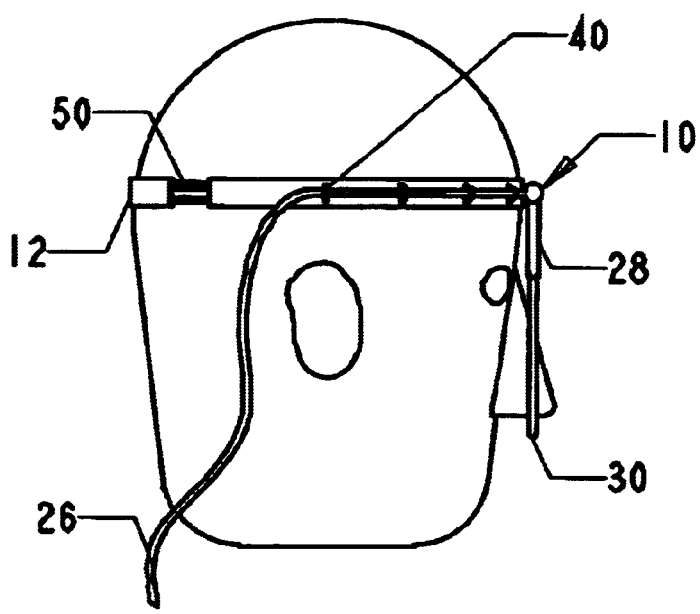
FIG. 3 shows a side view of the apparatus in use on a person.

FIG. 3 shows a side view of the cannula headband apparatus 10, again showing the headband 12 wrapped around a patient's head in a generally horizontal fashion. The cannula tube 26 is securely fastened to the headband 12 by at least one of the fasteners 40 and is positioned on the headband 12 such that the cannula tube 26 is held behind the patient's ear. The fasteners 40 direct the cannula tube 26 toward the cannula junction 28 such that the breathable gas is directed toward the patient's nose and into the patient's nostrils via nasal extensions 30. As also shown in FIG. 3, in one embodiment the headband 12 may be held around the patient's head by an elastic portion 50. As shown in FIG. 3, the headband connecting portion 50 may be positioned such that it is not directly behind the patient's head but instead is slightly to one side or the other.

Figure 4:
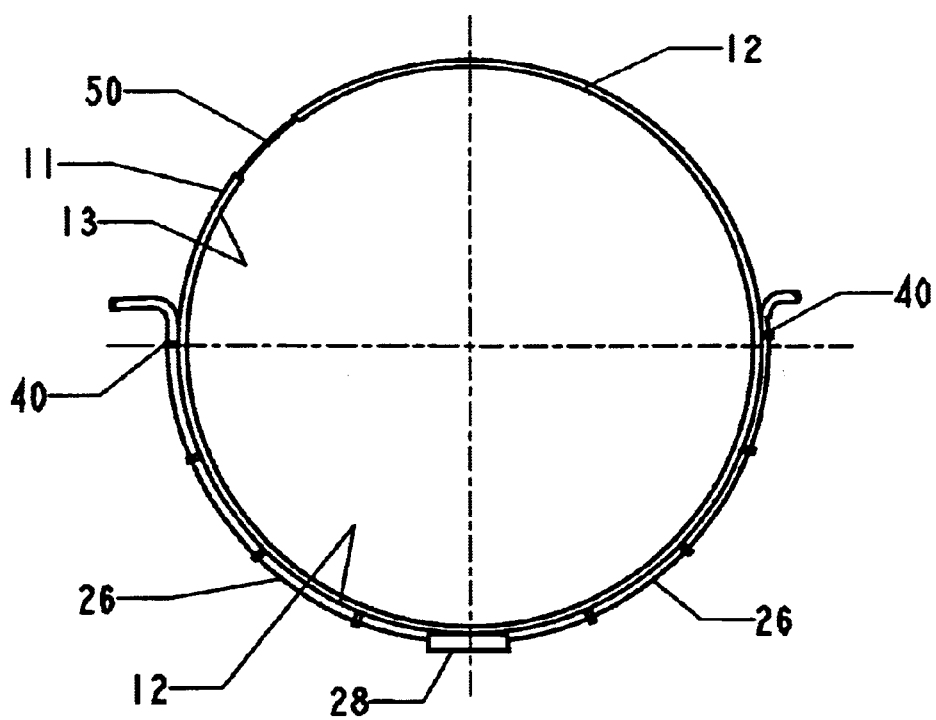
FIG. 4 shows a top view of the headband portion.

FIG. 4 shows a top view of the headband portion 12. The dash lines are shown to generally align the headband 12 with the patient's head. The patient's nose may be positioned below the cannula junction 28. As shown in FIG. 4, the headband 12 has an inner side 13 and an outer side 11. In one embodiment, the inner side 13 is made from a material that has a greater coefficient of friction than a material that is used on an outer side 11 of the headband 12. The material on the inner side 13 of the headband 12 may be able to facilitate the holding of the headband 12 about the patient's head. The outer side 11 may be made from a material having a smoother surface such that the outer side 11 slides more easily about a pillow, sheet, or other bedding material brushed up against it. The headband 12 material is designed such that as the user sleeps, the material on the outer side 11 allows the headband to slide about the bedding, and the material on the inner side 13 helps secure the headband 12 to the user's head such that the headband stays in place while the user sleeps. As also seen in FIG. 4, the cannula tubes 26 are connected to the outer side 11 of the headband 12 by fasteners 40. In the example of FIG. 4, the headband 12 is also held in place on a user's head by a headband connecting portion 50, which is positioned on a rear side of a user's head.

Figure 5:
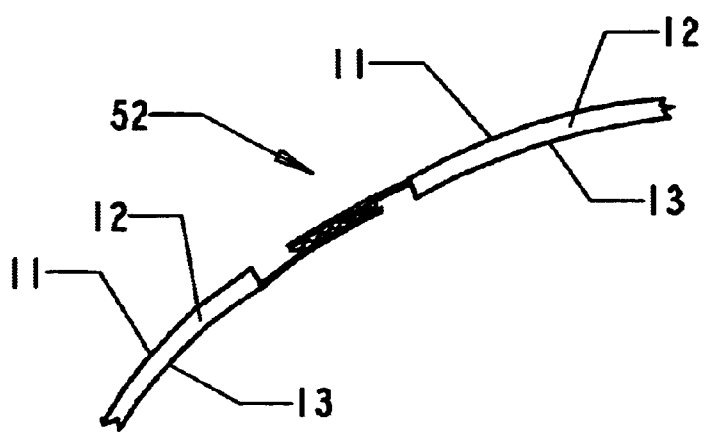
FIG. 5 shows one means of connecting the headband portion around a user's head.

FIG. 5 shows an alternative embodiment of the headband-connecting portion 50 that uses a hook-and-loop connector 52, such as a Velcro strap. In the embodiment of FIG. 5, the headband 12 may be made from a non-elastic material, and the fastening portion 52 may hold the headband 12 securely about the patient's head.

Figure 6:
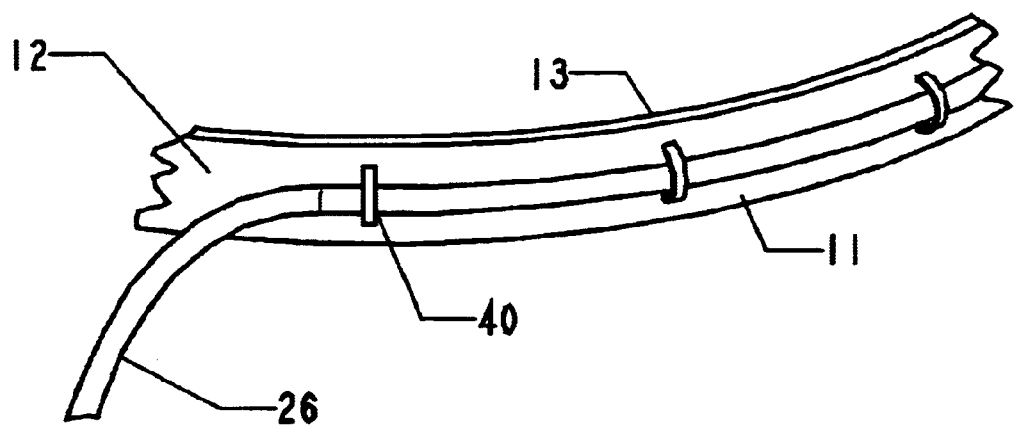
FIG. 6 shows a connection between the cannula tube and the headband portion.

FIG. 6 shows a more detailed diagram of the connection between the cannula tube 26 and the headband 12. As shown in FIG. 6, the fasteners 40 securely hold the cannula tube 26 to the outer side 11 of the headband 12. The inner side 13 of the headband 12 faces the patient's head. The fasteners 40 hold the cannula tube 26 in such a manner that the tube is allowed to drape down behind the user's ear, where it is out of the patient's way.

Figure 7:
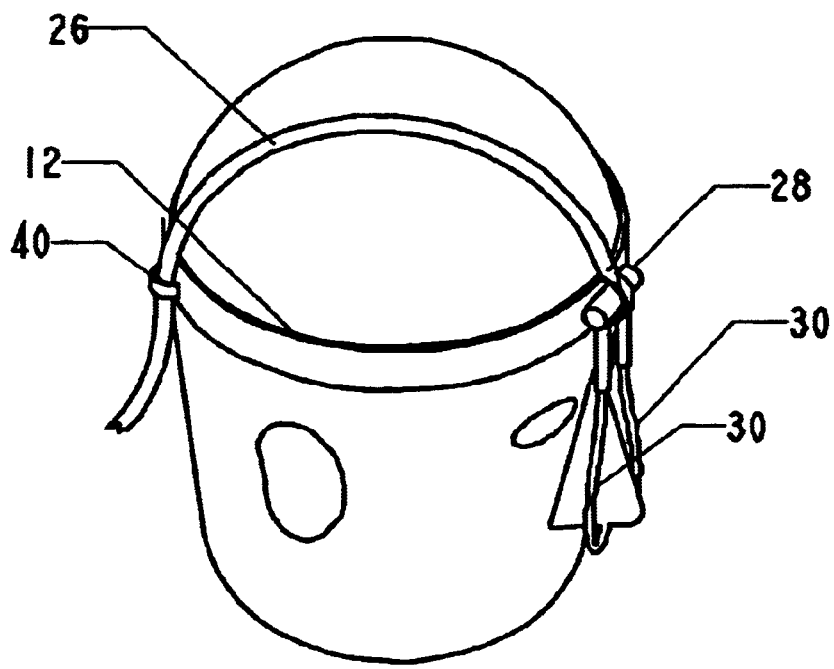
FIG. 7. shows an alternative embodiment of the apparatus in use on a person.

FIG. 7 shows an alternative embodiment of the cannula apparatus 10 in which one or more cannula tubes 26 pass over the top or crown portion of a user's head. In the embodiment shown in FIG. 7, a single cannula tube 26 is connected to a cannula junction 28 positioned above a user's nose and fixedly attached to the headband 12, which is held in place along the circumference of a user's head above the ears. The cannula junction 28 is connected to nasal extensions 30 that deliver the gas to a user's nostrils. The cannula tube 26 is fixedly attached to the cannula junction 28, or directly to the headband 12 by a fastener (not shown). In the embodiment shown, the cannula tube 26 runs substantially over the top of a user's head and connects to the rear portion of the headband 12. The cannula tube 26 may be connected to the rear portion of the headband 12 near the center of the back of a user's head. The cannula tube 26 is connected by a fastener 40 that holds the tube 26 in place by a friction fit, but allows the user to move the cannula tube 26 relative to the headband 12 to adjust for a wearer's head. For example, the user may slideably adjust the cannula tube(s) 26 relative to the fastener to achieve a desired fit.

Figure 8:
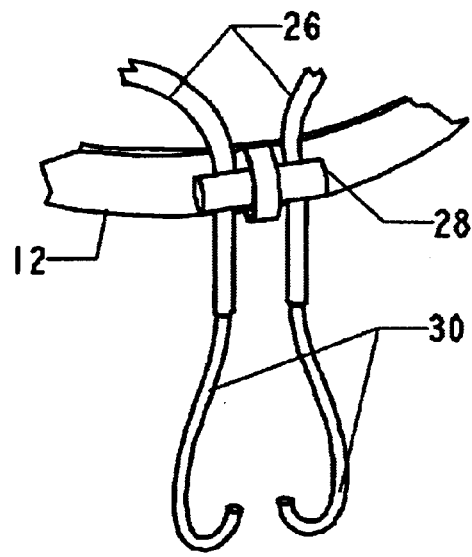
FIG. 8. shows the connection of a front portion of the embodiment of the apparatus shown in FIG. 7.

FIG. 8 shows a more detailed view of the front portion of the headband 12 in the embodiment shown in FIG. 7, in which the cannula tube 26 is attached to the front and rear of the headband and passes over the user's head. In the embodiment shown in FIG. 9, the apparatus uses two cannula tubes 26, which connect to a cannula junction 28 that is secured to the front of the headband 12. The cannula junction 28 receives a gas such as air from the cannula tubes 26 and communicates that gas to the user's nose via nasal extensions 30.

Figure 9:
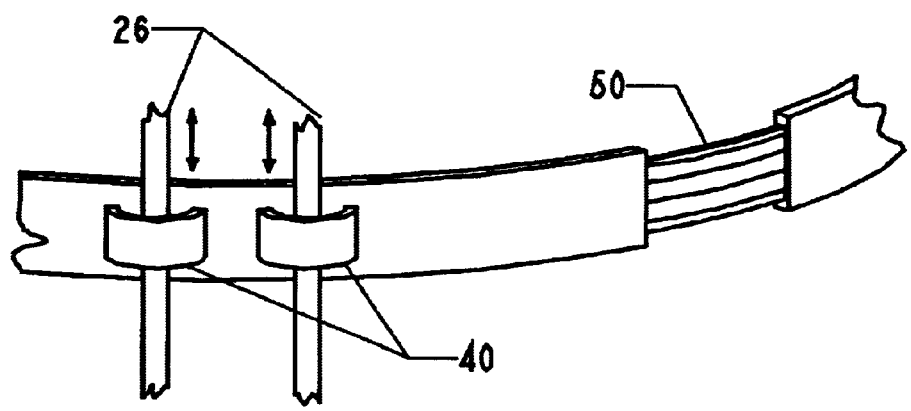
FIG. 9. shows the connection of a back portion of the embodiment of the apparatus shown in FIG. 7.

FIG. 9 shows the rear portion of the embodiment of the apparatus shown in FIG. 7. In the example of FIG. 9, two cannula tubes 26 pass over the top of a wearer's head and connect to the back portion of the headband 12 by separate fasteners 40. The connection to the rear of the headband holds the tubes 26 in place, but allows them to move relative to the headband 12, as indicated by the arrows, upon exertion of a force by the user. This allows adjustment of the cannula tube 26 length between the front of the headband 12 and the rear—that is, the length passing over the top of a wearer's head. This allows the tubes 26 to be adjusted to different head sizes and to make a connection more or less snug. In the embodiment of FIG. 9, the cannula tubes 26 connect to the rear of the headband 12 at substantially the center of the back of the wearer's head. As shown in FIG. 9, the connecting portion 50 of the headband 12 is offset from the connection of the cannula tubes 26 to the headband 12 in one embodiment.

Figure 10:
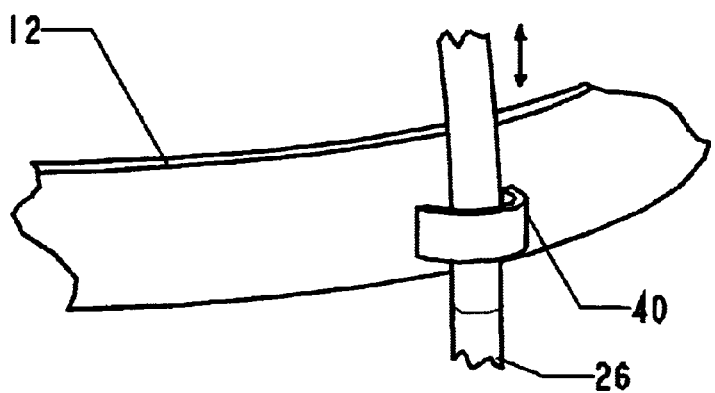
FIG. 10. shows another embodiment of the back portion of the embodiment shown in FIG. 7.

FIG. 10 shows the rear portion of the cannula headband 12 in an alternative embodiment. In the embodiment of FIG. 10, a single cannula tube 26 passes over the top of a user's head and connects to the rear of the headband 12 using two fasteners 40. The fasteners 40 slidably connect the cannula tube 26 to the headband 12 in such a manner that the cannula tube 26 stays in place while the user is wearing the apparatus but may be adjusted. In another embodiment, the fasteners 40 hold the cannula tube(s) 26 loosely to permit the cannula tube(s) 26 to move relative to the headband 12 as the user moves.

Although the present invention has been described with respect to particular embodiments thereof, variations are possible. The present invention may be embodied in specific forms without departing from the essential spirit or attributes thereof. It is desired that the embodiments described herein be considered in all respects illustrative and not restrictive and that reference be made to the appended claims and their equivalents for determining the scope of the invention.

I claim:

1. A nasal cannula apparatus comprising:
   a headband adapted for being worn around a circumference of a person's head, the headband having an inner side and an outer side; and
   a cannula system fixedly connected to the outer side of the headband such that the entire cannula system is positioned outside of the headband, the cannula system comprising:
   a pair of cannula tubes, each of said tubes having an inlet end and an outlet end;
   a cannula junction connected to the outlet end of the cannula tubes; and
   a pair of nasal extensions connected to the cannula junction.

2. The apparatus of claim 1, wherein the headband is constructed of a soft and lightweight material and has a width of 1.5 inches to 2.0 inches.

3. The apparatus of claim 1, wherein the outer side of the headband is smooth and aids in keeping the headband on a person's head when the headband brushes against fabric, such as bedding.

4. The apparatus of claim 1, wherein the headband is made from a fabric that is water resistant, whereby the headband maintains its shape when wet.

5. The apparatus of claim 1, wherein the headband has a non-elastic fabric portion, and a connecting portion connected to the fabric portion, which connecting portion secures the headband to the person's head by creating a tension in the headband.

6. The apparatus of claim 1, wherein the pair of cannula tubes, the cannula junction, and the pair of nasal extensions are separate, removably connected members.

7. The apparatus of claim 1, wherein the cannula tubes are fixedly connected to the outer side of the headband by a plurality of fasteners.

8. The apparatus of claim 7, wherein the fasteners hold the cannula tubes in place along a length of the headband such that the cannula tubes run along a front portion of the circumference of the person's head.

9. The apparatus of claim 8, wherein the plurality of fasteners comprises fasteners positioned along the length of the headband from the front of the headband near the cannula junction toward the rear of the headband away from the cannula junction, and wherein the rear-most fasteners are positioned near the person's ears when worn on the person's head, such that the cannula tubes are held away from the person's ears when in use.

10. A nasal cannula apparatus comprising:
    a headband adapted for being worn around a circumference of a person's head, the headband having an inner side and an outer side; and
    a nasal cannula system fixedly connected to the outer side of the headband, the nasal cannula system comprising a cannula tube fixedly connected by a plurality of connectors to the outer side of the headband such that the cannula tube runs generally parallel to the headband along the circumference of a person's head when in use, the plurality of connectors comprising:
    a first connector that connects the cannula tube to the headband near a person's nose when in use;
    a second connector that connects the cannula tube to the headband near a person's ear when in use, such that the cannula tube is directed behind a user's ear.

11. The apparatus of claim 10, wherein the headband comprises a single strip of soft, lightweight, water-resistant material having first and second ends each having a width of between 1 inch and 2.5 inches, and has a length approximately equal to the circumference of the person's head, and a connecting portion connected to the first and second ends which connecting portion holds the headband tight against the user's head.

12. The apparatus of claim 11, wherein the outer side of the headband is smooth and aids in keeping the headband in place on a person's head when the headband brushes against fabric.

13. The apparatus of claim 10, wherein the outer side of the headband is smooth, whereby the outer side aids in keeping the headband in place on a person's head when the headband brushes against fabric.

14. The apparatus of claim 10, wherein the cannula tube is a flexible plastic tubing having an inside diameter between 0.0625 inches and 0.25 inches.

15. The apparatus of claim 10, wherein the cannula system is connected to the headband such that the nasal cannula tube is positioned entirely outside of the headband.

16. A nasal cannula apparatus comprising:
   a headband; and
   a nasal cannula system fixedly connected to the headband such that the cannula system is positioned entirely outside of the headband, comprising:
      a trunk cannula having an inlet end capable of connecting to a source of a gas and an outlet end;
      a trunk connector connected to the outlet end of the trunk cannula;
      a cannula tube having an inlet and an outlet end, the inlet end being connected to the trunk connector;
      a cannula junction connected to the outlet end of the cannula tube;
      a pair of nasal extensions each having an inlet end and an outlet end, the extensions being connected to the cannula junction at the inlet ends of the extensions and the outlet ends being open and capable of being directed toward a nose of a user, whereby the gas may be directed from the source to the outlet ends of the nasal extensions through the cannula system.

17. The apparatus of claim 16, wherein the headband is adapted for being worn around a circumference of a user's head and comprises a single strip of soft, lightweight, water-resistant material having first and second ends each having width a of between 1 inch and 2.5 inches and has a length approximately equal to the circumference of the person's head, and a connecting portion that connects the first and second ends to each other and holds the headband tight against the user's head.

18. A nasal cannula apparatus comprising:
   a headband adapted for being worn around a circumference of a person's head, the headband having an inner side and an outer side; and
   a cannula system fixedly connected to the outer side of the headband, the cannula system comprising:
      a pair of cannula tubes, each of said tubes having an inlet end and an outlet end;
      a cannula junction connected to the outlet end of the cannula tubes; and
      a pair of nasal extensions connected to the cannula junction,
   wherein the cannula tubes are fixedly connected to the cannula junction and are slidably connected to a rear portion of the headband wherein that the cannula tubes pass over a top portion of the person's head when in use, and wherein the cannula tubes slidably adjust to the person's head.

19. A nasal cannula apparatus comprising:
   a headband; and
   a nasal cannula system fixedly connected to the headband, comprising:
      a trunk cannula having an inlet end capable of connecting to a source of a gas and an outlet end;
      a trunk connector connected to the outlet end of the trunk cannula;
      a cannula tube having an inlet and an outlet end, the inlet end being connected to the trunk connector;
      a cannula junction connected to the outlet end of the cannula tube;
      a pair of nasal extensions each having an inlet end and an outlet end, the extensions being connected to the cannula junction at the inlet ends of the extensions and the outlet ends being open and capable of being directed toward a nose of a user, whereby the gas may be directed from the source to the outlet ends of the nasal extensions through the cannula system,
   wherein the cannula tube is fixedly connected to the cannula junction and is slidably connected to a rear portion of the headband such that the cannula tube passes over a top portion of the person's head when in use, wherein the cannula tube slidably adjusts to the person's head.

20. The apparatus of claim 19, wherein the cannula tube provides support for the headband to keep it in place on the user's head.

21. A nasal cannula apparatus comprising:
   a headband adapted for being worn around a circumference of a person's head, the headband having an inner side and an outer side; and
   a cannula system fixedly connected to the outer side of the headband, the cannula system comprising:
      a pair of cannula tubes, each of said tubes having an inlet end and an outlet end;
      a cannula junction connected to the outlet end of the cannula tubes; and
      a pair of nasal extensions connected to the cannula junction,
   wherein the pair of cannula tubes, the cannula junction, and the pair of nasal extensions are formed from as a single, contiguous piece of material.

* * * * *